United States Patent [19]

Lewis

[11] Patent Number: 4,640,128

[45] Date of Patent: Feb. 3, 1987

[54] MECHANISM FOR PROPER ALIGNMENT OF SENSOR PROBES WITH FLUID SAMPLE CHAMBER

[75] Inventor: Terry D. Lewis, Aptos, Calif.

[73] Assignee: The Kendall Company, Boston, Mass.

[21] Appl. No.: 683,989

[22] Filed: Dec. 20, 1984

[51] Int. Cl.⁴ .................. G01D 3/04; G01D 21/00; G01N 9/24

[52] U.S. Cl. .................. 73/866.5; 128/767; 73/32 A; 73/1 R

[58] Field of Search .......... 73/1 R, 32 A, 432 B, 73/432 R, 863, 863.21, 863.71, 863.81, 864, 864.51; 128/630, 762, 760, 767, 768, 771

[56] References Cited

U.S. PATENT DOCUMENTS

| | | | |
|---|---|---|---|
| 3,371,524 | 3/1968 | Wloszek | 73/1 R X |
| 4,314,484 | 2/1982 | Bowman | 73/861.41 |
| 4,327,586 | 5/1982 | Goddard | 73/432 B |
| 4,418,565 | 12/1983 | St. John | 73/19 |
| 4,432,231 | 2/1984 | Napp et al. | 73/290 V |

FOREIGN PATENT DOCUMENTS

446809  9/1975  U.S.S.R. .................. 73/32 A

Primary Examiner—Stewart J. Levy
Assistant Examiner—Tom Noland
Attorney, Agent, or Firm—Donald N. Halgren

[57] ABSTRACT

Apparatus for correctly aligning a pair of sensor probes relative to a sample chamber location in a biological fluid sensor apparatus for sensing fluid in a sample chamber. The sensor probes are carried at the end of a pair of arms mounted for pivotal movement toward one another and the sample chamber location. The distance between these sensor probes when sensing with different sample chamber assemblies of possibly different dimensions established by a blocking member which blocks the arms from movement toward one another beyond a preselected limit. The sensor probe assembly includes a transducer assembly with a transducer housing having a tip and a transducer mounted in a sensing position at the tip together with a guide assembly having a guide housing and structure for mounting the transducer assembly protectively therewithin for relative movement between an inoperative position and an operative position. In the inoperative position, the tip is protectably recessed within the probe guide, and in an operative position, the probe tip protrudes from the guide for sensing engagement with the sensor wall. The sample chamber assembly is provided with a female guide receptical which has a first portion for mating receipt of the guide assembly to guide it into a correct position for receipt of the protruding probe tip by an access opening of the female guide receptical which is located opposite a sensor wall of the chamber.

22 Claims, 15 Drawing Figures

MECHANISM FOR PROPER ALIGNMENT OF SENSOR PROBES WITH FLUID SAMPLE CHAMBER

BACKGROUND OF THE INVENTION

This invention relates to sensor probe assemblies and means for aligning same on opposite sides of a sample chamber.

In sensing of the specific gravity of a biological fluid, such as human urine, it is known to employ sensor probes which are held against or adjacent the sides of a sample chamber at a preselected chamber location. The distance between a pair of probes is not necessarily critical to accuracy for all types of sensing, such as photoelectric sensing shown in U.S. Pat. No. 4,343,316 of Jesperson and entitled "Electronic Urine Flow Monitor". However, when accurate sensing relies upon the speed of conduction of ultrasonic pulses between a pair of transducers, it is critical that such distance remain the same for repeated measurements employing different sample chamber assemblies of possibly different dimension.

It is known to maintain this distance by mounting both the transducers in a stationary fixture. For example, in U.S. Pat. No. 4,418,565 of St. John, entitled "Ultrasonic Bubble Detector", the probes are held fixed on opposite sides of a channel of a probe housing. Flexible tubing conveying the flow being monitored for bubbles conforms to the channel shape when it is pressed into the channel and between the probes fixedly held thereby. The housing defines the channel and thus determines the distance between the probes.

This approach, unfortunately, offers little in the way of a solution when the sensor probes must be movably mounted for relative engagement and disengagement with different sample chambers. In such a system, the probes must be movably mounted between operative sensing positions in which they are engaged with opposite sides of a single chamber to an inoperative position in which they are separated further apart from one another and disengaged from the sampling chamber. It is necessary to be able to reliably and repeatedly precisely align the sensor probes with different sampling chambers assemblies of possibly different dmensions while still protecting the probe with a suitable housing. Concurrently, the distance between the probes must remain the same for all measurements regardless of dimensional differences between the sampling chambers.

SUMMARY OF THE INVENTION

Thus, it is the principal object of the present invention to provide a solution to this problem and, in particular, to provide an apparatus for correctly aligning a pair of sensor probes with a sample chamber on a repeatedly reliable basis and to provide a sensor probe assembly employable with such an apparatus and having a protective housing.

In keeping with this objective, I provide an apparatus for correctly aligning a pair of sensor probes relative to a sample chamber location in a biological fluid sensor apparatus for sensing fluid in the sample chamber. The aligning apparatus comprises a pair of arms for carrying the pair of sensor probes, means for mounting the arms for movement of the probes toward one another, means for blocking the arms for movement toward one another beyond a preselected limit and means for moving the arms into blocking engagement with the blocking means. Thus, the distance between the probes is established by the blocking member which remains the same and not in any way by the sample chamber dimensions or the dimensions of any protective housing for the sensor probes.

In a preferred embodiment, the arms are mounted for pivotal movement toward one another about a pair of spaced pivotal axes, and means linking the arms together causes them to symmetrically pivot toward and away from each other and the sample chamber location from opposite sides thereof.

It is also an object to provide this apparatus in combination with a sensor chamber having a pair of flexible sensor walls for respective engagement by the sensor probes. Advantageously, the neutral planes of such sensor walls when unflexed are spaced from one another by a preselected distance which is slightly greater than the distance between the probes when the arms have been moved to the preselected limit. Accordingly, when the arms are moved to the preselected limit the sensor probes press against the sensor walls which conform thereto and, as noted above, the distance between the probes is determined solely by the preselected limit. The flexibility of the sample chamber walls prevents the different dimensions of the sample chamber from interfering with establishment of the preselected distance by the alignment apparatus.

The principal object is further achieved by provision of a sensor probe assembly comprising a transducer assembly including a transducer housing with a tip and a transducer mounted in a sensing position at the tip together with a guide assembly including a guide housing and means for mounting the transducer assembly protectively therewithin for relative movement between an inoperative position and an operative position. In the inoperative position, the tip is protectively recessed within the probe guide, and when in an operative position, the probe tip protrudes from the guide for sensing engagement with an object, such as a sensor wall, to be sensed outside of the guide assembly.

In a preferred embodiment, the chamber has a pair of connector members for guiding receipt of the probes. The sensor probes and guide members are configured relatively to one another to cause a symmetrical engagement of the pair of guide members by the pair of probes to correctly align the chamber relative to the probes for proper sensing. In one embodiment, the mating surfaces of the guide housing and guide members are spherical and in another embodiment they are conical.

Actuation of the alignment apparatus is achieved through means of an actuation member mounted for movement between closed and open position, and means for linking the actuation member to the arms for causing them to move together against the blocking means. Preferably, means are provided for restraining the moving means from moving the arms away from one another at too high of a speed during disengagement.

BRIEF DESCRIPTION OF THE DRAWINGS

The foregoing objects, features and advantages of the present invention will be described in greater detail and further objects and advantageous features will be made apparent in the following detailed description of the preferred embodiment which is given with reference to the several figures of the drawing, in which.

DETAILED DESCRIPTION

Figure 1:
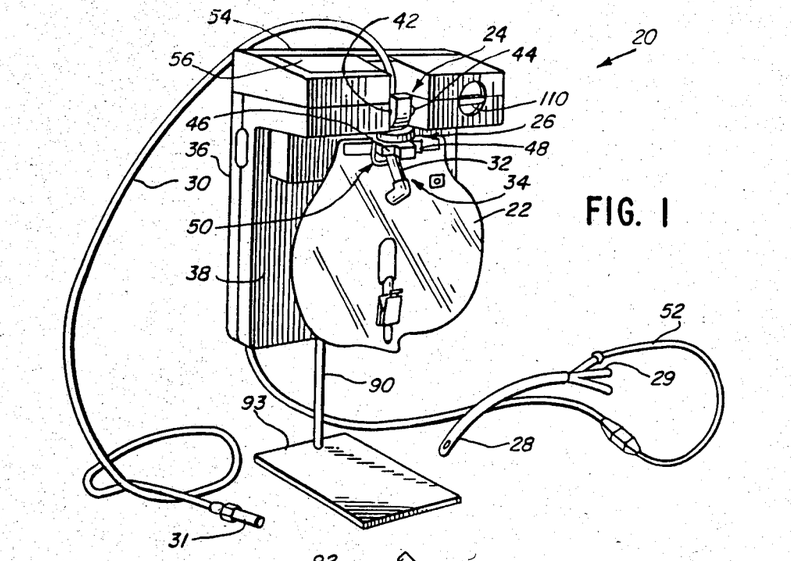
FIG. 1 is a perspective view of an automated urine output monitor, or AUOM, for weighing and making other measurements of urine collected in a flexible urinary collection bag releasibly attached thereto and with respect to which a preferred embodiment of the present invention is employed.
Figure 2:
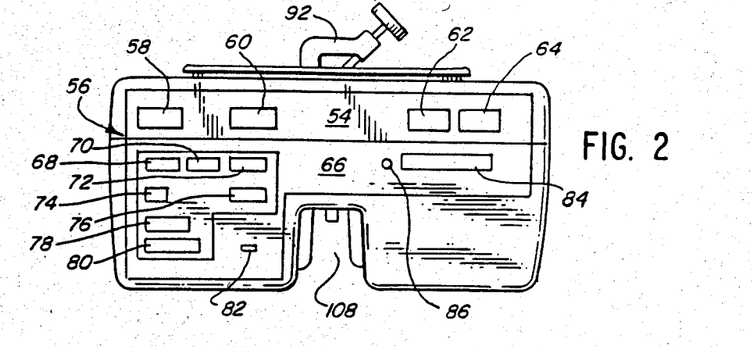
FIG. 2 is a plan view of the AUOM of FIG. 1 showing the AUOM display and control panel.

Referring now to the several figures of the drawing, particularly FIGS. 1 and 2, an automated urinary output monitor, or AUOM, 20 is seen with a flexible, plastic urinary collection bag 22 mounted thereto by means of a sampling chamber assembly 24 and a force isolation system 26. As will be explained in greater detail, the sampling chamber assembly 24 and force isolation system 26 interconnect to form a closed fluid collection system between a patient (not shown) connected to the distal end of a Foley catheter 28 and the interior of the urinary collection bag 22. The catheter 28 is connectable by means of a catheter connector 29 and a catheter adapter 31 to one end of a flexible, plastic drainage tube 30. The other end of the drainage tube 30 is in fluid communication with the sampling chamber assembly 24 by means of a suitable tube connector located at its top. Fluid from sampling chamber assembly 24 flows through a flexible conduit of the force isolation system 26 and from there through an angular conduit 32 of a front entry connector assembly 34.

Still referring to FIG. 1, the AUOM is seen to have a housing, comprised of a housing frame 36 with a removable front housing panel 38. This housing protectively encloses an electronic control and measurement module (not shown) which includes a computer and interface circuitry. The computer receives signals through the interface circuitry from suitable transducers associated with a pair of sensor probe assemblies 42 and 44 connectable with the opposite sides of sampling chamber assembly 24 for noninvasively determining both specific gravity and temperature of a urine sample contained within the chamber assembly 24.

Figure 3:
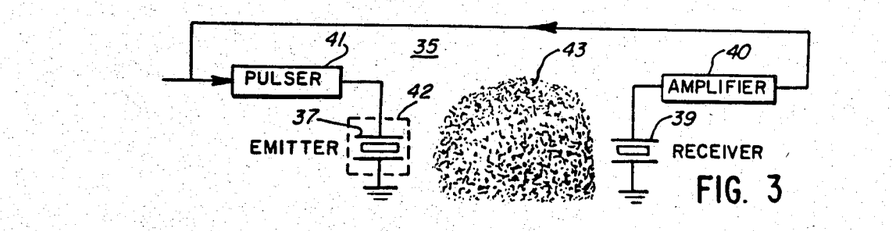
FIG. 3 is a schematic block diagram of the sensor circuit used in connection with sensor probes and the sampling chamber of FIG. 1.

Referring briefly to FIG. 3, the sensor probe assemblies 42 and 44 comprise part of an ultrasonic oscillating sensing circuit 35. The oscillator circuit 35 includes an emitting transducer, or emitter, 37 of sensor probe assembly 42 which emits ultrasonic pulses in response to electrical signals and a receiving transducer, or receiver, 39 of sensor probe assembly 44 for converting received ultrasonic pulses into corresponding electrical signals. The corresponding electrical signals are amplified by an amplifier 40 and applied through a feedback path to a pulser 41 which triggers the emitter 37. The speed at which the ultrasonic pulse is transmitted through the urine specimen, or other sample, 43 is a function of its specific gravity, and thus the frequency of the feedback signal of the oscillator circuit 35 is related to the specific gravity. This frequency of the sensing circuit 35 is fed to the computer which employs this information to calculate and display the specific gravity of the specimen.

The computer is also responsive to electronic signals received through other interface circuitry from transducers associated with a pair of mounting arms 46 and 48 of a bag mounting assembly 50 to determine the weight of the urine collected within urinary collection bag 22. The computer also determines core temperature based on signals from a core temperature probe (not shown) within catheter 28 and connected to the computer by an electrical cord 52. The computer also receives and responds to signals from a suitable transducer indicative of the ambient temperature, signals indicative of the status of its D.C. portable battery supply (not shown) and signals from a control section 54 of a control and display panel 56, as best seen in FIG. 2.

Referring particularly to FIG. 2, these controls include a manually actuatable reset switch 58, a start switch 60, a temperature scale selection switch 62 and a display light actuation switch 64. The computer automatically, periodically calculates specific gravity, temperature, volume and time based upon these transducer and control input signals and causes them to be visually indicated at various electronic digital display units of a display section 66 of control and display panel 56. The volume in milliliters of the urine collected in collection bag 22 total for the present hour, for the previous hour and for the entire collection period commencing with actuation of start switch 60, is indicated at display units 68, 70 and 72, respectively. Based upon appropriate signals received from either the start switch 60 or reset switch 58, and an internal clock, the computer also respectively indicates at display units 74 and 76, the number of minutes elapsed since the present hour commenced and the cumulative time since the current collection process started. The specific gravity is shown on display unit 78, and core temperature, either in Fahrenheit or centigrade degrees depending upon the state of scale selection switch 62, is shown at display unit 80. A low battery condition for the portable AUOM is provided by an indicator 82, and various conditions sensed by the computer are indicated by an alpha numeric message display unit 84 and an alert indicator lamp 86.

Further information concerning the operation of the computer, transducers, oscillating sensor circuit 35 and other related aspects of the AUOM unit 20 may be obtained by reference to the U.S. patent application Ser. No. 684,235, now abandoned and re-filed as Ser. No. 730,741, of Brian H. Silver entitled "Electronic Biological Fluid Output Monitoring With Noninvasive Sensing", U.S. patent application of Frank W. Ingle and Alan R. Selfridge entitled "Biological Fluid Specific Gravity Monitor with Ultrasonic Sensor Circuit", and U.S. patent application Ser. No. 683,981, now abandoned and re-filed as Ser. No. 731,140, of Fred M. Rasmussen entitled "Ultrasonic Sensor", all filed contemporaneously herewith and assigned to the assignee of this application.

In normal operations, the AUOM unit is releasibly attached to an upright mounting standard 90 by means of a screw clamp 92 attached to the back of housing 36. Although standard 90 may be mounted to its own floor supported base member 93, as shown, preferably, standard 90 is releasibly mounted to the patient's bed in a manner shown in U.S. patent application Ser. No. 684,238 of James R. Gross, entitled "Medical Equipment Mounting Apparatus" filed contemporaneously herewith and assigned to the assignee of this application.

The catheter set consists of the catheter 28, the catheter drainage tube 30, the sampling chamber assembly 24, the force isolation system 26, the front entry connector assembly 34 and the collection bag 22. After the AUOM unit has been mounted in a location near, but outside, the sterile fluid of the catherization site of the patient, the catherization set is brought to the patient and the patient is catherized. After the catherization procedure, the urinary collection bag 22 is taken to the AUOM unit 20 outside the sterile field and is there mounted by means of the bag mounting assembly 50 and the sensor probe assemblies.

Figure 4:
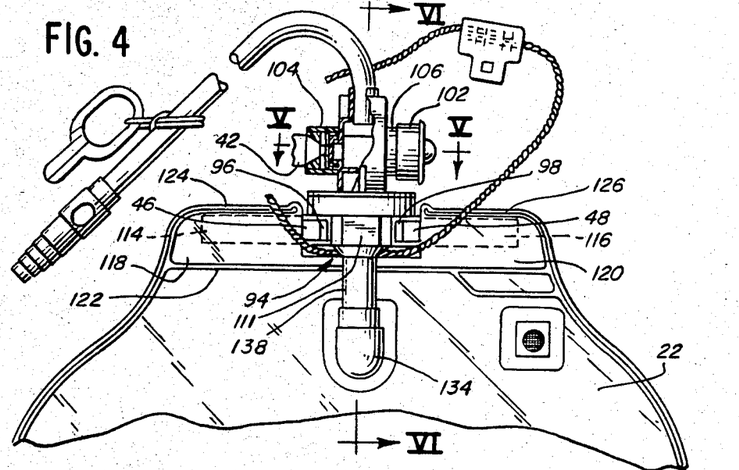
FIG. 4 is an enlarged front view of a header assembly and force isolation and sampling chamber assemblies connected with the urinary collection bag of FIG. 1.

Referring to FIG. 4, the force isolation system 26 includes a relatively rigid header assembly 94 having a pair of spaced female connectors 96 and 98 which are adapted for mating receipt of mounting arms 46 and 48, respectively, to suspend the collection bag 22 therefrom. Preferably, means are provided for causing arms 46 and 48 to releasably interlock with female connectors 96 and 98 as described in U.S. patent application Ser. No. 683,981, now abandoned and re-filed as Ser. No. 731,140 of Robert M. Sakai and William J. Dunn, entitled "Suspension Mounting Apparatus For Biological Fluid Collection Bag" filed contemporaneously herewith and assigned to the same assignee as this application.

The collection bag 22 is locked onto arms 46 and 48 after a pair of protective sensor caps, or covers, 102, only one of which is shown in FIG. 4, are removed from a pair of sensor probe guide connectors 104 and 106. The connectors 104 and 106 are mounted to a chamber of the sampling chamber assembly 24 having a sensing location. The connectors 104 and 106 are enabled for receipt of the sensor probes by removing the sensor caps 102.

Figures 5, 6, 7:
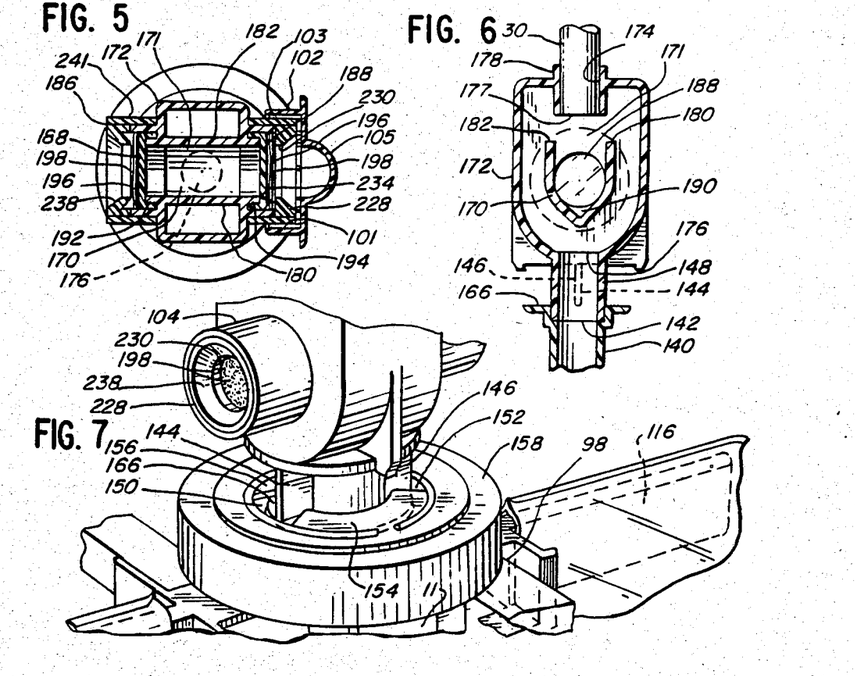
FIG. 5 is a sectional plan view of the sampling chamber assembly taken along section line V—V of FIG. 4.
FIG. 6 is a sectional side view of the sampling chamber assembly taken along section line VI—VI of FIG. 4.
FIG. 7 is an enlarged perspective view of the force isolation and sampling chamber assembly of FIGS. 1, 2 and 4–6.

The connectors 104 and 106 are mounted opposite a pair of relatively flexible sensor walls 186 and 188, FIG. 5, of the sampling chamber assembly 24. Each of the connectors 104 and 106 has an access opening opposite one of the sensing locations of these sensor walls 186 and 188 for receipt of sensor probe assemblies 42 or 44, FIG. 1. The sensor caps 102 cover these access openings and protect the sensing locations.

Also, once caps 102 are removed, the sampling chamber assembly 24 is enabled for receipt within a sensing location 108 with sensor probe guide connectors 104 and 106 respectively engaged with sensor probe assemblies 42 and 44. Each of the sensor covers 102 has a blocking member 105 which has a lateral dimension sufficient to block insertion of the sampling chamber assembly 24 into the sensing location 108 when either one of the covers 102 is attached to its associated connector.

Figures 11, 13:
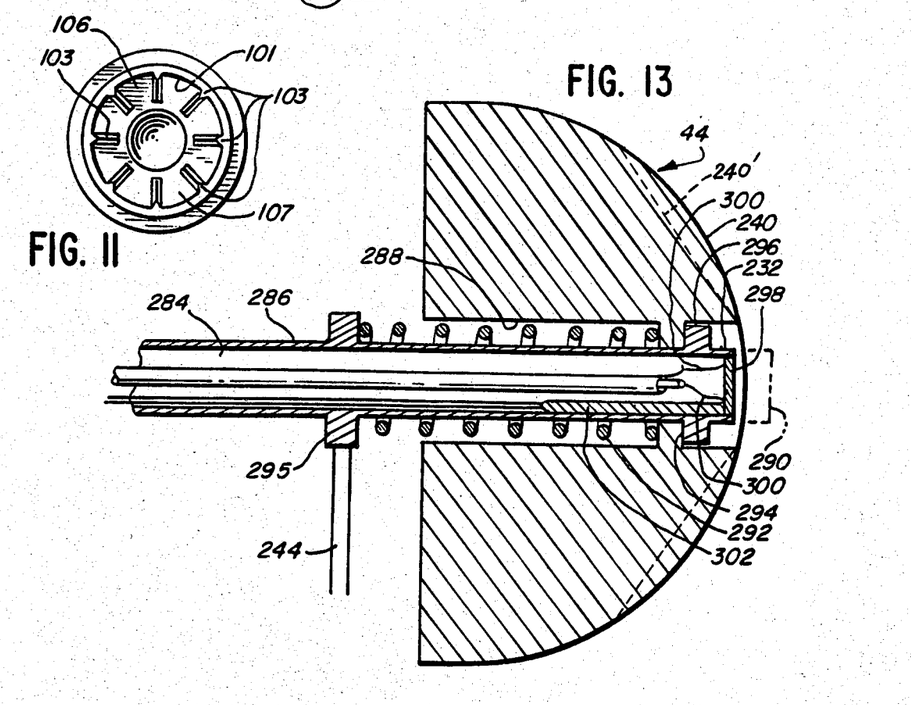
FIG. 11 is a plan view of the cap of FIGS. 4 and 5.
FIG. 13 is a sectional side view of the sensor probe assembly of FIG. 12 taken along section line XIII—XIII thereof.

Referring to both FIGS. 5 and 11, the interior wall 101 of cap 102 has a plurality of vanes, or ridges, 103 for preventing a gas tight seal with the probe guide connectors 104 and 106. These vanes 103 are also preferably extended to the interior surface of a top, or cover piece, 107 of the sensor cap 102, as best seen in FIG. 11. The gaps created by these vanes 103 provides gaseous access to the sensing locations and thereby enable the unit to be gas sterilized without removing the protective caps 102.

Before the collection bag 22 is locked onto arms 46 and 48, the sensor caps 102 are removed and the sampling chamber assembly 24 located in sensing location 108 between sensor probes 42 and 44. The two sensor probe assemblies 42 and 44 are then caused to move together through manual actuation of a probe actuator 110. When the actuator 110 is moved from a horizontal position to the operative position shown in FIG. 1, the two sensor probes move together and respectively matingly engage the sensor probe guide connectors 104 and 106, as will be explained in greater detail with reference to FIG. 12. This holds the sampling chamber assembly to the frame 36, and since the downstream, open end 177 of the drainage tube 30 is mounted to sampling chamber assembly 24, it is also held against any movement relative to the housing frame 36. After this is done, the start switch 60 is actuated and the AUOM unit 20 begins operations to provide the monitor information described above.

Referring particularly to FIGS. 4 and 7, the header assembly 94 is seen to comprise a central body 111 with a central force isolation header connector, or connector opening therethrough (not shown), located between the pair of female connectors 96 and 98 together with a pair of opposed header mounting arms 114 and 116. The header assembly 94 is secured to the flexible bag 22 by means of a pair of header mounting pockets 118 and 120 within which are held mounting arms 114 and 116, respectively. These pockets are formed from extensions of the back and front walls of urinary collection bag 22 which are secured together along a common seam 122 and a pair of upper seams 124 and 126 respectively associated with header mounting pockets 118 and 120.

The front wall of urinary collection bag 22 has an inlet opening in fluid communication with a coupler 134. A fluid conductive connector assembly, which forms part of the force isolation system 26, includes a downturned, elongate portion, or angular conduit, 138 for making fluid connection between the front of the flexible bag 22 through coupler 134. The other end of the angular conduit 138 is connected to a hopper portion of the force isolation system extending through the central body 111. This hopper portion, in turn, is in fluid communication with the sampling chamber assembly 24 through a highly flexible, diaphragmatic conduit contained within the force isolation system 26. The flexible conduit has one end connected to the hopper portion and its other end coupled to a connector 140 at the outlet 142 of the sampling chamber assembly 24, as best seen in FIG. 6.

As best seen in FIGS. 6 and 7, the force isolation system 26 includes means associated with the sampling chamber assembly 24 for restraining relative rotary movement between the ends of the flexible diaphragm which would twist it beyond a preselected limit. The rotary restraint is provided by means of a pair of radial blocking members 144 and 146 which are fixedly attached to an elongate conduit 148 of the sampling chamber assembly 24 which defines outlet 142 at its open end. The radial blocking members 144 and 146 are received within a pair of slots 150 and 152. Slots 150 and 152 are formed by a pair of opposed arcuate sections 154 and 156 of restraint portion 158 of the force isolation system 26. Each of arcuate sections 154 and 156 define a pair of rotary blocking surfaces which prevent the radial blocking members 144 and 146 associated therewith, and thus the flexible diaphragm of force isolation system 26, from rotary movement beyond a preselected limit.

The diaphragm connector 140 carries a stop member 166 which is engageable in blocking relationship with the underside of arcuate sections 154 and 156 to restrain the inlet and outlet connectors of the flexible diaphragm from relative movement beyond a preselected limit. Movement beyond this limit could cause the transmission of force to the header assembly 94 or would stretch or otherwise damage the diaphragm.

Further, information concerning the details and advantages of the force isolation system, such as the flexible diaphragm, the header assembly 94 and the mounting assembly 50 is obtainable by reference to the other U.S. patent applications filed contemporaneously herewith and assigned to the same assignee as this application, such as U.S. patent applications entitled "Apparatus With Force Isolation For Measuring Weight of Collected Fluid and Method" Ser. No. 684,234, now abandoned and re-filed as Ser. No. 730,740, of Brian H. Silver; "Force Isolation Apparatus With Limit Restraint For Fluid Collection System" Ser. No. 684,230, now abandoned and re-filed as Ser. No. 730,739, of Brian H. Silver and William J. Dunn; "Force Isolation Apparatus With Non-cylindrical Conduit For Biological Fluid Collection System" Ser. No. 684,237 of James R. Gross and William J. Dunn; "Connection Apparatus For Side Connection To Fluid Collection Bag" Ser. No. 683,993 of Lucien M. Rath and William J. Dunn; and "Suspension Mounting Apparatus of Biological Fluid Collection Bag" of Robert M. Sakai and William J. Dunn.

It should be appreciated in this regard that while in the preferred embodiment of the sampling chamber assembly, it has the features noted above which cooperate with and, in fact, form a part of the force isolation system, many of the other features and advantages of the sampling chamber assembly which will be described below are useable separate and apart from the force isolation system or parts associated therewith.

Referring again to FIGS. 5 and 6, the sampling chamber assembly 24 has a sampling chamber 170 attached to and contained within a sampling chamber housing 172 intermediate a housing inlet 174 and an outlet 176. The inlet 174 is connected in fluid communication with the open end 177 of drainage tube 30 by means of an annular inlet connector 178. After the flexible drainage tube 30 is inserted into mating relationship with connector 178, the connection is rendered permanent by means of applying adhesive, causing preapplied adhesive to set, solvent bonding or the like. The housing outlet 176 is connected to an inlet end of the elongate conduit 148. The outlet 142 of conduit 148 is coupled through means of the connector 140 with the flexible diaphragm connector of the force isolation system 26, as disclosed above and in the above referenced patent applications, to form a closed fluid collection system between the housing inlet 174 and the interior of the urinary collection bag 22.

As best seen in FIG. 6, the sampling chamber 170 is a trough-shaped member having an open top 171 defined in part by edges 180 and 182 of a pair of opposite walls of chamber 170. This open top 171 is situated at a position beneath the housing inlet 174, so that fluid from the open end 177 of drainage tube 30 falls into the open top 171 and the open top thus comprises an inlet for sampling chamber 170. New fluid entering this inlet replenishes and mixes with any fluid previously stored in the chamber. Once the fluid has filled sampling chamber 170, the addition of more fluid will cause some of the previously received fluid to overflow one or both of edges 180 and 182. Thus, the open top 171 also functions as an outlet for sampling chamber 170.

The opposite walls of the sampling chamber 170 are preferably integrally formed of plastic together with the sampling chamber housing 170, the annular inlet connector 178 and the elongate conduit 148. Preferably, the plastic is transparent, so the fluid in the chamber housing 172 and sampling chamber 170 is accessible to visual monitoring.

As noted above, the fluid sampling chamber has a pair of opposed, sensor walls 186 and 188. These walls also comprise exterior walls of the housing 172, so that they are accessible to sensors, such as ultrasonic emitter 37 of sensor probe assembly 42, located outside of the housing for making non-invasive measurements of characteristics of the fluid within the sampling chamber 170. Preferably, the distance between sensor walls 186 and 188 is selected for optimum sensing of the fluid being sensed. For sensing the specific gravity of human urine, a distance on the order of 1.0 inch has been found suitable for sensing with the ultrasonic "sing around" circuit of FIG. 3.

Since the fluid is continuously being replenished with fresh fluid during the collection process, continuous in-line measurements are made on fresh samples. Preferably, erroneous readings due to the accumulation of particulate matter settling out of suspension from the fluid are avoided by providing the sampling chamber with a sediment trap 190 located beneath the sensing level of the sensor walls 186 and 188.

The sensor walls 186 and 188 preferably comprise relatively thin, flexible, resilient membranes which are mounted to the relatively rigid bosses 192 and 194, respectively, to close circular sensor wall openings at the opposite sides of sampling chamber housing 172 and sampling chamber 170. These membranes are made from flexible plastic, or other suitable material which has an ultrasonic transmission characteristic comparable to that of the fluid being sensed. For sensing human urine, urethane plastic of 5 mils thickness has been found to be suitable.

When the sampling chamber 170 is employed with a sensor probe assembly 44, such as shown in FIG. 13, which has a temperature sensor, described below, the flexible sensor walls 186 and 188 are selected to have a relatively high heat conduction characteristic which is not substantially less than that of the remainder of the walls of chamber 170. Sensor walls made of the plastic noted above have been found suitable for this purpose.

Figure 10A:
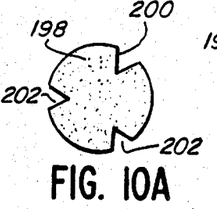
FIGS. 10A and 10B are schematic illustrations of alternate embodiments of the coupling agent distribution member of the sampling chamber assembly of FIGS. 5 and 7.
Figure 10B:
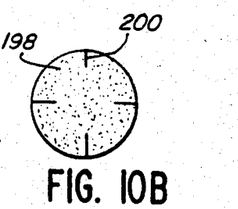

Referring to FIGS. 10A and 10B in addition to FIG. 6, an acoustic coupling agent assembly is provided to enhance good airless coupling between the sensor probe assemblies 42 and 44 and the sensor walls 186 and 188. This assembly comprises a fluid acoustic coupling agent 196 at the outside surface of the sensor walls 186 and 188 and a relatively thin coupling agent distribution member 198 overlying the sensor wall 186 or 188. The thin distribution member 198 is preferably made of coupling agent-absorbent, flexible, paper-like, material. If so, some of the fluid coupling agent 196 is absorbed within the distribution member. Preferably, the coupling agent 196 is a fluid such as an oil-like substance, or silicon fluid. For acoustic coupling with sensor walls 186 and 188 made of material having acoustic transmission characteristics matched to human urine, the use of silicone fluid, such as Dow 710, made by Dow Chemical Company for the coupling agent and use of paper such as used for tea bags as the distribution member 198 has been found satisfactory.

With respect to the configuration of the thin distribution member 198, it is a disc with a generally circular shape which matches that of the sensor probe assemblies 42 and 44 and the sensor walls 186 and 188. Preferably, the thin distribution member 198 has cuts 200 which form pie-shaped notches 202, as shown in FIG. 10A, or which simply form radial slits, as shown in FIG. 10B. These cuts have been found to facilitate the flexible movement of the thin distribution member 198 with that of the sensor wall 186 or 188 to avoid wrinkling and possible resultant air gaps.

Referring to FIGS. 5 and 7 again, a relatively rigid connector member 228 is mounted to the chamber assembly 24 around each of the sensor walls 186 and 188. These connectors 228 have an access opening 230 for coupling engagement therethrough of a transducer, or probe, tip 232, shown in FIG. 13, of sensor probe assembly 44 of FIG. 1. In addition, connector 228 includes an annular shoulder portion 234 in retentive overlying relationship with the acoustic coupling agent assembly including the coupling agent 196 and the relatively thin coupling agent distribution member 198. This shoulder portion 234 simply blocks the distribution disc 198 from passage through the access opening 230 or the fluid coupling agent 196 from flowing out of the access opening 230 and away from adjacency to the sensor wall 186 or 188. The diameter of the distribution disc 198 is greater than that of the access opening 230.

Figure 12:
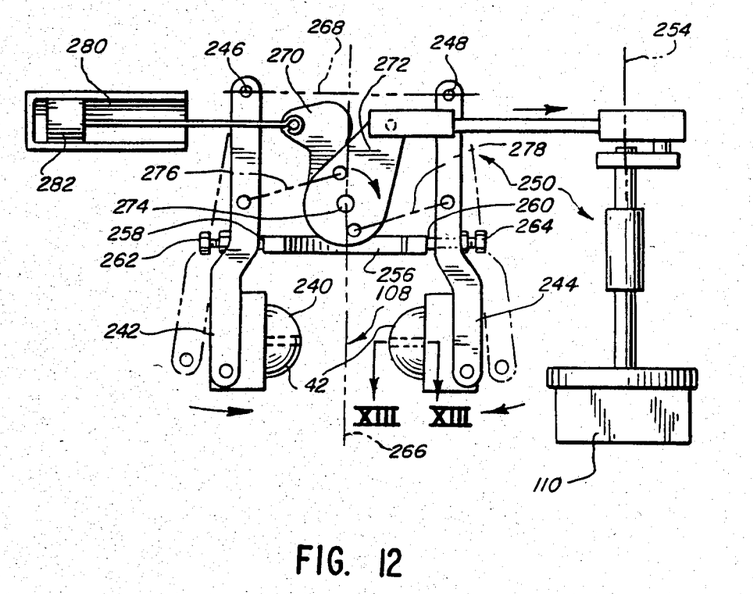
FIG. 12 is a schematic plan view of the sensor probe alignment mechanism of FIG. 1.

The connector member also has a partially spherical guiding surface 238 for guiding and then snugly seating the forward part of a partially spherical probe housing, or guide, 240 of sensor probe assembly 42 to a position in which the probe tip 232 is directly opposite and insertable through the associated access opening 230, as seen in FIGS. 12 and 13. As the sensor probe assemblies 42 and 44 are moved together to their operative position, the guide surfaces 238 being engaged by the spherical probe housing 240 causes the access opening 230 to automatically become aligned with the probe tips 232. The connector also has an exterior cylindrical connector surface 241 for releasable mating connection with protective sensor cap 102.

Figure 8A:
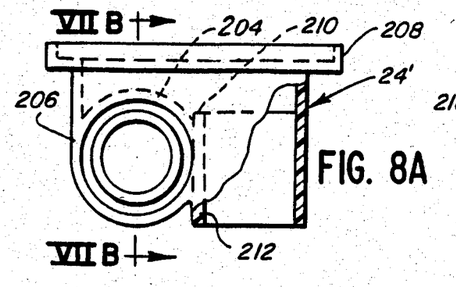
FIG. 8A is a side view, partially in section, of an alternate embodiment of the sampling chamber assembly of FIGS. 4–7.
Figure 8B:
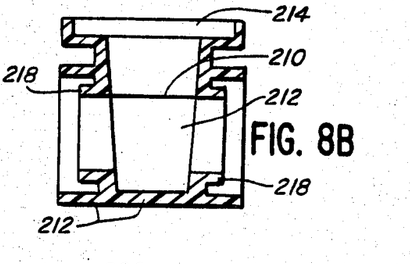
FIG. 8B is a sectional front view of the chamber assembly of FIG. 8A taken along section line VIIIB—VIIIB thereof.
Figure 9:
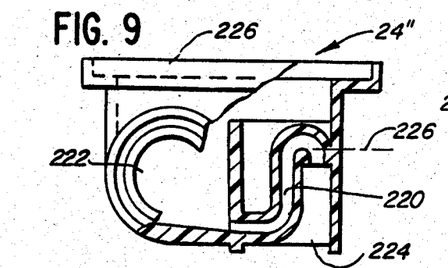
FIG. 9 is a sectional side view of yet another embodiment of the sampling chamber assembly of FIGS. 4–7.

The acoustic coupling agent assembly of FIGS. 5, 6, 10A and 10B is also employable with the other forms of the sampling chamber assembly 24' and 24" shown in FIGS. 8A-8B, and 9, respectively. These sampling chamber assemblies 24' and 24" are structurally identical and used in a substantially identical fashion as the sampling chamber assembly 24 of FIGS. 5 and 6, except as indicated.

Chamber assembly 24' is constructed differently in that its top 204 is defined partly by one of the walls 206 of chamber assembly housing 208 and partly by the edge 210 of a chamber wall 212. Accordingly, fluid collection in the chamber is free to flow over only the one edge 210 once the chamber of assembly 24' is overfilled. However, as with chamber assembly 24, the sampling chamber 24' is partly defined by a pair of flexible sensor walls (not shown) which are mounted to close the openings defined by a pair of bosses 218.

The chamber assembly 24" of FIG. 9 is different from both of the chamber assemblies 24 and 24', in that it includes an inverted U-shaped siphon tube 220. Unlike the other chamber assemblies 24 and 24', this siphon tube 220 causes the entire fluid contents of sampling chamber 222 to be periodically, automatically flushed out of the chamber and through the tube 220 and an outlet 224 when the fluid level reaches the level 226 of the inverted U-portion of the siphone tube 220. As in sampling chamber assembly, all fluid passes through the sampling chamber 222, since there is no alternative communication between the inlet 227 and the outlet 224.

Referring to FIG. 12, the sensor probe assembly 42 and 44 are carried at the ends of a pair of arms 242 and 244, respectively, mounted for pivotal motion about a pair of pivot axes 246 and 248, respectively. A mechanical linkage 250 between the probe actuator 110 converts rotary movement of the actuator 110 about an axis 254 into translational movement of the arms 242 and 244 and sensor probe assemblies 42 and 44 toward one another. Movement of the arms toward one another beyond a preselected limit, however, is prevented by a rigid blocking member 256. Blocking member 256 has a pair of arm engaging blocking surfaces 258 and 260 which are in blocking relationship with the associated arms 242 and 244. The blocking surfaces 258 and 260 are spaced from one another by a distance substantially corresponding to the preselected limit. Fine adjustments are made by a pair of adjustment screws 262 and 264 which are adjustably mounted to arms 242 and 244 and engageable with blocking surfaces 258 and 260. Generally, however, the blocking surfaces 258 and 260 are equidistantly located on opposite sides of a center plane 266 extending perpendicularly from a line 268 intersecting the axis of the pair of arms.

The mechanical linkage 250 includes a pair of cranks 270 and 272 with a common axis 274 and linkage arms 276 and 278 pivotally connected to arms 242 and 244. This linkage causes arms 242 and 244 to symmetrically pivot toward and away from one another at opposite sides of the sensing location 108.

A dash pot 280 with its piston 282 linked to crank 270 prevents damage to sensor probe assemblies 42 and 44 by excessively rapid movement. The dash pot 280 prevents this rapid movement of arms 242 and 244 when they are being moved from their operative position, as shown in solid line, to their inoperative position, shown in broken line. The dash pot 280, however, does not significantly restrain movement in the opposite direction.

Referring now to FIG. 13, each of the sensor probe assemblies 42 and 44 includes a sensor probe 284. Sensor probe 284 has a transducer housing 286 which is slideably received within an axial bore 288 of the probe assembly housing 240 at one end. The other end is connected to and carried by the appropriate one of arms 242 and 244 of FIG. 12 at the other end. As noted above, the sensor probe housing 240 and guide surface 238 complementarily match one another to cause the symmetrical engagement of the pair of female guide surfaces 238 of connector member 228 by the probe housing to correctly align the chamber assembly 24 relative to the probes for proper sensing.

While spherical surfaces for the probe housing 240 and guide surface 238 work fine, conical surfaces such as surface 240', FIG. 13, will work as well or better to achieve the desired automatic alignment through engagement.

After the mating engagement of the probe housing 240 with the guide surfaces 238 stops further relative movement therebetween, the sensor probe housings 286 continue to move toward one another until the arms 242 and 244 are blocked against further movement when the preselected distance is reached. As they continue to move, each of the probes slideably move within its associated bore 288 from an inoperative position in which the probe tip 232 is protectively recessed within the bore 288, as shown in FIG. 13 in solid line, to an operative position 290, shown in broken line, in which the probe tip 232 protrudes from the end of the probe guide housing 240. An annular collar 296 of transducer housing 286 resiliently seats against shoulder 294 when it is in its inoperative position. A coil spring 292 bears against a collar 295 at the end of arm 244 or 242 and a collar 296 of transducer housing 286 to resiliently bias the probe toward its protected, inoperative position. Accordingly, when the probe guide 240 is disengaged from guide surface 238, it automatically recedes within the bore 288.

The sensor walls 186 and 188, when in an unflexed state, are spaced from one another by a preselected distance which is slightly greater than the distance between the probe tips when they have been moved to the preselected distance established by blocking member 256. Accordingly, the probe tips 232 resiliently press thereagainst to assist in the removal of any gaps therebetween. Thus, the blocking member 256, and not the sampling chamber assembly dimensions, establishes the preselected distance between the probe tips. This critical distance can therefore be maintained constant for different measurements with different sampling chambers despite minor variations in the distances between the sensor walls.

The transducer, when an ultrasonic transducer is used, comprises an ultrasonic crystal disc mounted at the end of probe tip 232 to close the opening at the end of housing 286. If it is the emitter 37, electrical signals are applied to the crystal disc 298 via a pair of leads 300 to cause ultrasonic vibrations of the disc 298. If it is the receiver 39, vibrations of the disc 298 are converted thereby to electrical signals which are connected to the amplifier 40 of FIG. 3.

In addition to the acoustic transducer, a temperature sensing transducer 302, such as a thermistor, is mounted within probe housing 286 as seen the end of the probe is in physical contact with the interior side of disc 298 and thus senses the temperature of the sensor walls and fluid through the disc 298. This speeds response time but does not significantly interfere with the ultrasonic transducing characteristic of the disc 298. Preferably, the temperature transducer 302 is contained within the receiving transducer probe housing 286, and the disc and sensor walls are selected to have corresponding heat conduction characteristics.

While a preferred embodiment has been illustrated in detail for purposes of making full disclosure of the best mode, the scope of invention for which patent protection is sought is set forth in the following claims.

What is claimed is:

1. In a biological fluid sensor apparatus for sensing fluid in a sample chamber, an apparatus for correctly aligning a pair of sensor probes relative to a sample chamber location, comprising:
   a pair of arms for carrying the pair of sensor probes;
   means for mounting the arms for movement of the probes toward one another;
   means for blocking the arms from movement toward one another beyond a preselected limit; and
   means for moving said arms into blocking engagement with said blocking means.

2. The sensor apparatus of claim 1 in which the arms are mounted for pivotal movement toward one another about a pair of spaced pivotal axes.

3. The sensor apparatus of claim 2 including means for mounting said blocking member with its ends equidistantly located on opposite sides of a center plane extending perpendicularly from a line intersecting the pivot axes of the pair of arms.

4. The sensor apparatus of claim 1 in which said blocking means comprises a single rigid blocking member having a pair of spaced arm engaging ends which are spaced from one another by a distance corresponding to said preselected limit.

5. The sensor apparatus of claim 1 including means linked with both of said arms for causing them to symmetrically pivot toward and away from each other and the sample chamber location from opposite sides thereof.

6. The sensor apparatus of claim 1 in combination with
   a chamber having a pair of female connector guide members for receipt of said sensor probes into engagement therewith, and in which
   the probes and guide members are configured relative to one another to cause the symmetrical engagement of the pair of guide members by the pair of probes to correctly align the chamber relative to the probes for proper sensing.

7. The sensor apparatus of claim 6 in which said probe has a conical surface.

8. The sensor apparatus of claim 5 in which said linked means includes a manually engageable member.

9. The sensor apparatus of claim 1 in combination with
   a sensor chamber having a pair of flexible sensor walls for respective engagement by said pair of sensor probes, the neutral planes of said sensor walls when unflexed being spaced from one another by a preselected distance which is slightly greater than the distance between the probes when the arms have been moved to the preselected limit, and including
   means for moving said arms to the preselected limit to cause the distance between the probes during sensing to be determined by the preselected limit and not by the sample chamber.

10. The sensor apparatus of claim 1 including
means linked with the arms for moving said arms to said preselected minimum limit; and
means for releasibly holding said arm at the limit.

11. The sensor apparatus of claim 1 in combination with a sample chamber supportively held between the pair of probes pressed thereagainst when the arms are at the preselected limit.

12. The sensor apparatus of claim 1 including means for restraining the arm moving means from moving the arms away from one another at too high of a speed during disengagement.

13. The sensor apparatus of claim 12 in which said restraining means including a dash pot and means for mechanically linking the arms to the dash pot.

14. The sensor apparatus of claim 1 including
an actuation member;
means for mounting said actuation member for movement between closed and open positions; and
means for linking said actuation member to the arms for causing them to move together against the blocking means.

15. The sensor apparatus of claim 14 including means for restraining said movement causing means from moving the arms apart at a speed faster than a preselected speed.

16. The sensor apparatus of claim 14 including means for providing detents for said actuation member.

17. The sensor apparatus of claim 14 in combination with
a pair of female guide receptacles for guiding said probes into a preselected sensing position; and
means for restraining the rate of movement of said sensor probes.

18. The sensor apparatus of claim 14 in which said actuation member is manually engageable for movement between its closed and opened positions.

19. The sensor apparatus of claim 1 including means for selectively adjusting said preselected limit.

20. The sensor apparatus of claim 19 in which said adjusting means includes means for selectively adjusting the limit of movement of both arms indpendently of one another.

21. The biological fluid sensor probe of claim 1 including
a probe guide; and
means for mounting said transducer for relative slideable movement between an inoperative position in which the tip is protectively recessed within the probe guide and an operative position in which the probe tip protrudes from the guide housing.

22. The biological fluid sensor probe of claim 21 including means mounted within the probe guide for resiliently biasing said housing and probe guide toward the inoperative position.

* * * * *